United States Patent [19]
Colak

[11] Patent Number: 6,023,341
[45] Date of Patent: Feb. 8, 2000

[54] DEVICE FOR AND METHOD OF FORMING AN IMAGE OF A TURBID MEDIUM

[75] Inventor: Sel B. Colak, Eindhoven, Netherlands

[73] Assignee: U.S. Philips Corporation, New York, N.Y.

[21] Appl. No.: 08/909,915

[22] Filed: Aug. 12, 1997

[30] Foreign Application Priority Data

Aug. 14, 1996 [EP] European Pat. Off. .............. 96202283

[51] Int. Cl.$^7$ .................................................. G01N 21/00
[52] U.S. Cl. ........................................... 356/435; 356/446
[58] Field of Search ................................... 600/476–478; 352/128, 131; 5/601, 607, 610; 356/432–435, 244, 246, 445–446; 378/18

[56] References Cited

U.S. PATENT DOCUMENTS

| | | | |
|---|---|---|---|
| 5,441,054 | 8/1995 | Tsuchiya | 356/39 |
| 5,477,051 | 12/1995 | Tsuchiya | 356/432 |
| 5,526,118 | 6/1996 | Miyagawa et al. | 356/349 |
| 5,596,987 | 1/1997 | Chance | 600/476 |

FOREIGN PATENT DOCUMENTS

| | | |
|---|---|---|
| 0643121A1 | 3/1995 | European Pat. Off. . |
| WO9523961 | 8/1995 | WIPO . |
| WO9638758 | 12/1996 | WIPO . |

OTHER PUBLICATIONS

"Monte Carlo Simulations of Photon Migration Path Distributions in Multiple Scattering Media", By S. Feng et al, SPIE, vol. 1888, 1993, pp. 78–89.

*Primary Examiner*—Robert Kim
*Attorney, Agent, or Firm*—Dwight H. Renfrew, Jr.

[57] ABSTRACT

A device for imaging a turbid medium, for example a breast of a female, includes a holder for receiving the medium, a light source, a photodetector and a processing unit for deriving the image from the intensities measured. The holder is adapted to receive besides the turbid medium also an adaptation medium for influencing a photon path distribution of the turbid medium. The use of different values of optical parameters of the adaptation medium introduces different photon path distributions in the turbid medium. By means of these different photon path distributions the resolution of the image can be improved by utilizing the light sources and/or photodetectors in the same positions. When a liquid is used as the adaptation medium the shape of the adaptation medium can be perfectly matched between the holder and the turbid medium.

14 Claims, 4 Drawing Sheets

DEVICE FOR AND METHOD OF FORMING AN IMAGE OF A TURBID MEDIUM

RELATED APPLICATION

This application is related in subject matter to a commonly owned application Ser. No. 08/909,917 naming as inventors Dimitrios Papaioannou, Gert W. 't Hooft, and Martinus B. Van Der Mark, which is filed simultaneously with and has the same title as this application, which application is incorporated herein by reference.

BACKGROUND OF THE INVENTION

1. Field of the Invention

The invention relates to a device for imaging a turbid medium, the device comprising a holder for receiving the turbid medium, a light source for irradiating the turbid medium, a photodetector for measuring the intensity of the light emanating from the turbid medium, and a processing unit for deriving an image of the turbid medium from the intensities measured.

The invention also relates to a method of forming an image of a turbid medium, which method includes the following steps: irradiating a turbid medium by means of light at a plurality of positions, measuring the intensity of the light emanating from the turbid medium at a plurality of positions, and deriving an image of the turbid medium from the intensities measured.

2. Description of Related Art

For the purpose of this patent application, a light source is intended to mean a source of electromagnetic radiation with a wavelength in the visible or infra-red range approximately between 500 and 1000 nm.

A device and method of this kind are known from WO 95/23961. The known device is used for imaging an internal structure of biological tissue. In medical diagnostics the known device could be used for imaging the internal structure of breast tissue of a human female. For example, a growth of a tumor can be localized in such an image of the internal structure of breast tissue. The resolution of the image formed by means of the known device is determined by, inter alia, the number of positions of the light source and the number of positions of photodetectors in which the intensity is measured. It is a drawback of the known device that the resolution can be enhanced only by providing additional light sources and/or photodetectors, so that the manufacture of the known device becomes more complex.

SUMMARY OF THE INVENTION

It is an object of the invention to enhance the resolution of the image of the internal structure of the turbid medium by utilizing the light sources already present in the existing positions. To this end, the device in accordance with the invention is characterized in that the holder is also arranged to receive an adaptation medium for influencing a photon path distribution in the turbid medium. Alternatively, the holder may be provided with an element having a adjustable reflection index. In this application, the photon path distribution represents the influence of a small absorbing object on the measured light when the absorbing object is placed at a position between the source and the photodetector of a particular source detector combination. The invention is based on the recognition of the fact that the properties of the adaptation medium can influence the propagation of light in the turbid medium, so that the photon path distribution between the light source and the photodetector can be adjusted in the turbid medium. By means of these different photon path distributions the resolution can be improved by utilizing the light sources and/or photodetectors in the same positions. Generally speaking, in an infinite uniform turbid medium contours of equal density in the photon path distribution between the light source and the photodetector have an ellipsoid-like shape. The heart line of the photon path distribution is defined as the highest probe probability and represents the highest influence on the light density at the photodetector when a small absorbing object is placed at a position at that line. In an infinite turbid medium the heart line coincides with the major axis of the ellipsoid and corresponds to a connecting line between the light source and the photodetector. In a semi-infinite turbid medium a deviation from said ellipsoid shape of the photon path distribution occurs and the heart line of the photon path distribution will be curved. The shape of the photon path distribution can be influenced by changing a value of an optical parameter of the adaptation medium, e.g. the reflection index or the absorption coefficient. The intensities associated with various heart lines in the turbid medium can be measured by repeating measurements with different values of the optical parameter of the adaptation medium. The change of the heart line of the photon path distribution in successive measurements is comparable to a change of the heart line of the distribution as caused by, for example a displacement of the light source and/or photo-detector along the boundary of the turbid medium during successive measurements.

Another device in accordance with the invention is characterized in that the holder is arranged to comprise a liquid as the adaptation medium. As a result, the shape of the adaptation medium can be matched perfectly with the turbid medium; the photon path distribution can be influenced by a choice of the optical parameters e.g. the absorption parameter $\mu_a$ and the transport or reduced scattering parameter $\mu_s'$ of the liquid. A description of the absorption parameter $\mu_a$ and the transport or reduced scattering parameter $\mu_s'$ can be found in, inter alia, Monte Carlo Simulations of Photon Migration Path distributions in Multiple Scattering Media, by S. Feng et al, SPIE, vol 1888, 1993, page 78–89.

A further device in accordance with the invention is characterized in that the light source is adapted to generate light having a substantially constant intensity. This has the effect that simple photodetectors and low frequency electronic circuits could be used in the device. In several prior art devices for imaging of turbid media a modulated light source is employed and therefore expensive photo-multiplier tubes and high frequency electronics circuits are necessary for the detection of light emanating from the turbid medium.

The invention also relates to a device for forming an image of a turbid medium, the device comprising a holder for receiving the turbid medium, a light source for irradiating the turbid medium, a photodetector for measuring the intensity of the light emanating from the turbid medium, and a processing unit for deriving an image of the turbid medium from the measured intensities, characterized in that the device comprises an element having an variable reflection coefficient with respect to the turbid medium. The reflection coefficient is one of the optical parameters of the adaptation medium which can be adjusted with respect to the turbid medium so as to influence the shape of the photon path distribution, thus enabling adjustment of the heart line in the turbid medium. A further advantage consists in that it is now possible to form an image of an internal structure of the turbid medium situated between the connecting line of the light source and the photodetector and the boundary of the turbid medium, without displacement of the light source and the photodetector being required.

The further embodiment of the device in accordance with the invention is characterized in that the adaptation medium comprises a liquid crystal device. The use of a liquid crystal device offers the advantage that no mechanical displacements are required for adjustment of the reflection coefficient with respect to the turbid medium. The reflection coefficient is adjusted by applying an electric voltage across the liquid crystal screen.

A further device in accordance with the invention is characterized in that the liquid crystal device comprises a cholesteric mirror. The use of a cholesteric device eliminates to use in a separate mirror in the adaption medium.

The invention also relates to a method of forming an image of a turbid medium, characterized in that a photon path distribution in the turbid medium is influenced by means of an adaptation medium.

The further method in accordance with the invention is characterized in that for influencing the photon path distribution in the turbid medium a dye is added to the liquid. As a result the absorption coefficient $\mu_a$ of the liquid could be easily adjusted with relation to the optical parameters of the turbid medium.

A further method in accordance with the invention is characterized in that for influencing the photon path distribution in the turbid medium a commercially available suspension for cosmetic purposes is used. An advantage of such a commercially available suspension for cosmetic purposes, e.g. a body milk, as the adaptation medium is that the body milk is thoroughly tested on the absence of harmful effects on the skin of a human body and likely to be readily accepted by any person to be investigated.

These and other aspects of the invention will be apparent from and elucidated with reference to the embodiments described hereinafter.

DETAILED DESCRIPTION OF THE PREFERRED EMBODIMENTS

Figure 1:
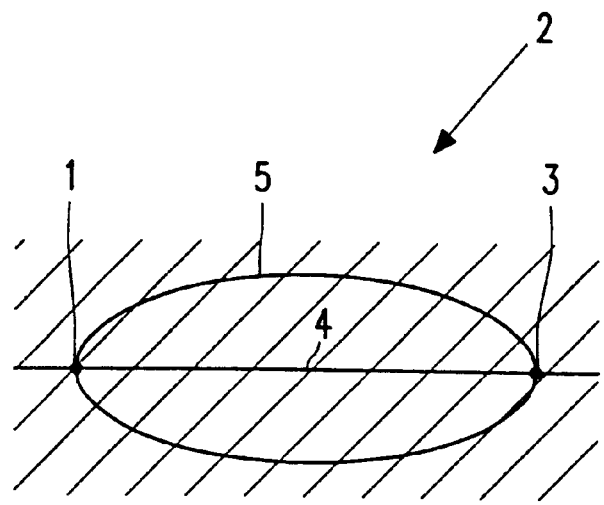
FIG. 1 shows a photon path distribution in a homogeneous turbid medium.

FIG. 1 shows, by way of example, the photon path distribution between a light source 1 and a photodetector 3 in an infinite homogeneous turbid medium 2. The photon path distribution is used to describe the transport of light in a turbid medium from a particular source to a particular detector. This description is known from, inter alia, Monte Carlo Simulations of Photon Migration Path distributions in Multiple Scattering Media, by S. Feng et al, SPIE, vol 1888, 1993, page 78–89. The contours of equal density of the photon path distribution in the infinite homogeneous turbid medium 2 correspond to ellipsoid-like shapes, like the one indicated by 5 in FIG. 1, a major axis 4 of which coincides with the heart line of the photon path distribution. The photon path density function peaks along this line between the light source and the photodetector and it is along this line that tissue contributes most to the detected light. Curved lines further outward correspond to lower photon path densities.

Figure 2:
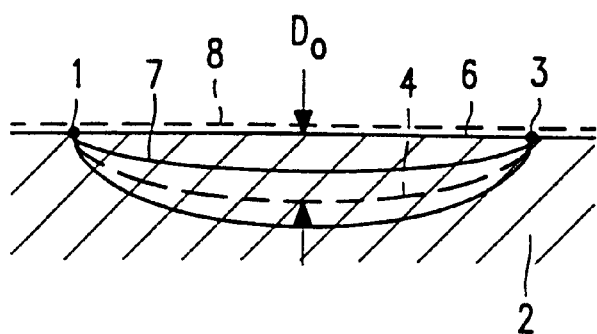
FIG. 2 shows a photon path distribution in a semi-infinite turbid medium.
Figure 3:
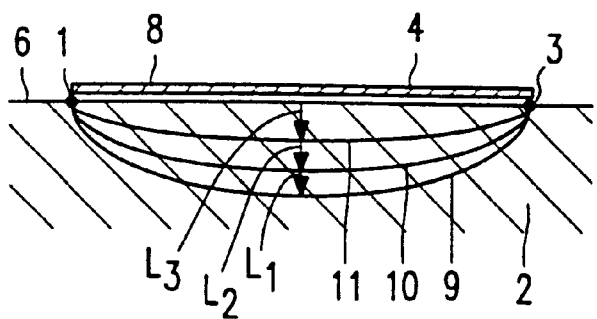
FIG. 3 shows various heart lines between light source and photodetector in a turbid medium different properties of the adaptation medium.

However, if a semi-infinite medium is used and the light source 1 and the photodetector 3 are situated at some distance from one another on the boundary surface 6, the shape of the photon path distribution will be distorted by photons leaving the turbid medium. FIG. 2 shows a distorted photon path distribution 7 in a semi-infinite turbid medium 2. The reference $D_o$ in FIG. 2 denotes the distance between the deflection of the heart line of the photon path distribution and the connecting line between the light source 1 and the photodetector 3. As is shown in FIG. 2 the heart line 4 of the distorted photon path distribution has been deflected with respect to the connecting line between the light source 1 and the photodetector 3, i.e. towards the interior of the turbid medium 2. The invention relates to the arrangement of an adaptation medium 8 along the boundary surface 6 of the turbid medium 2 in order to influence the heart line 4. An optical parameter, for example, the reflection coefficient of the adaptation medium 8 or the absorption coefficient of the adaptation medium, influences the quantity of photons leaving the turbid medium 2 via the boundary surface 6. The shape of the photon path distribution 5 between the light source 1 and the photodetector 3 in the turbid medium 2 thus changes. FIG. 3 illustrates the change of the center of the heart line for different values $R_j$ of the reflection coefficient on the boundary surface 6. As is shown in FIG. 3 the heart line of the photon path distribution is deflected away from the boundary surface for a decreasing reflection coefficient. In FIG. 3 the distance between the connecting line and the heart line is denoted with L. If the reflection coefficient of the adaptation medium 8 has approximately the value zero said distance L has the value $L_1$. If the reflection coefficient has a fixed value $R_1$ in the range between 0 and 1, said distance L has the value $L_2$ with $L_2<L_1$. If the reflection coefficient has a second fixed value $R_2$ in the range between $R_1$ and 1, said distance L has the value $L_3$ with $L_3<L_2$ and if the reflection coefficient has a value of approximately 1, said distance L becomes approximately 0.

The change of the shape of the photon path distribution as a function of the effective reflection coefficient of the adaptation medium and the turbid medium can be utilized in accordance with the invention in an optical mammography device for enhancement of the resolution of a reconstruction image of an internal structure of a turbid medium. An advantage of the invention is that mechanical displacement of the light source and/or the photodetector is not required, thus saving time during the execution of measurements. Another advantage of the invention is that installation of additional light sources and photodetectors is not necessary, so that the device remains less complex and easier to manufacture.

Figure 4:
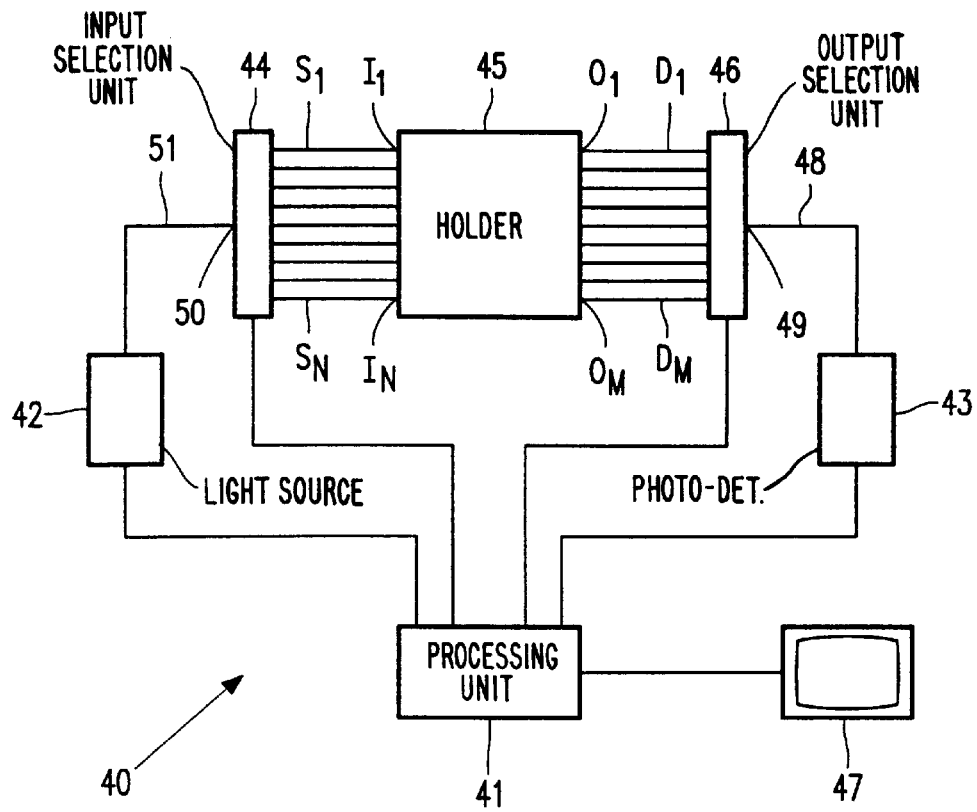
FIG. 4 shows a mammography device for forming an image of an internal structure of e turbid medium.
Figure 5:
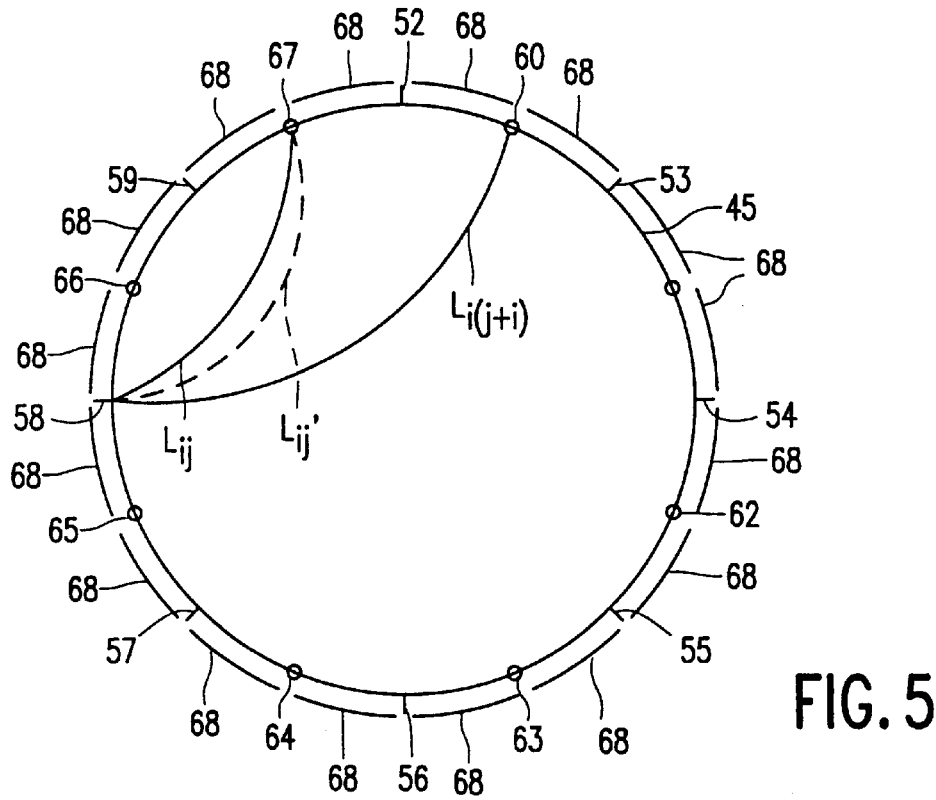
FIG. 5 shows the various light paths $L_{i,j}$ and $L_{i,j}'$ for different values of the reflection coefficient of the adaptation medium.

The invention will be described with reference to the FIGS. 4 and 5. FIG. 4 shows a mammography device 40.

The device in accordance with the invention has been described, by way of example, for a mammography system, but it can likely be used also for examination of other parts of a human or animal body. The device is intended to detect inhomogeneities in the tissue of a female breast. Examples of such inhomogeneities are increased microvascularizations or a high concentration of small blood vessels around a malignant tumor. The device in accordance with the invention is arranged to image such anomalies when they are still very small, so that a carcinoma can be discovered at an early stage, however, without subjecting the patient to the risks of examination by means of ionizing radiation, for example X-rays.

The mammography device in accordance with the invention is provided with a holder 45 which is arranged to receive a part of a breast, and also an adaptation medium. The mammography device 40 also comprises a light source 42 for generating light, a photodetector 43, a processing unit 41 for deriving an image from the measured intensities, and a monitor 47 for the display of images. The generated light may have either a substantially constant intensity or an amplitude-modulated intensity and a wavelength being in the range between, for example 500 and 1000 nm. The light source may comprise, for example a semi-conductor laser or light emitting diode. Another possibility is that the light source comprises of several semi-conductor lasers, each semi-conductor laser having a different wavelength in the interval between 500 and 1000 nm, and a selection switch to select one of the semi-conductor lasers. This arrangement allows to obtain optimal contrast of a reconstructed image for different optical characteristics of the turbid medium.

The photodetector 43 is arranged for detecting the light which may be coupled with the turbid medium via the output ports $O_1 \ldots O_M$ and an optical conductor 48. The photodetector 43 may comprise, for example a photomultiplier tube or a PIN photodiode. Other configurations with relation to the photodetectors are also possible. For example, a configuration, in which each of the output ports $O_1 \ldots O_M$ is coupled to a separate photodetector and the outputs of the photodetectors are measured in parallel. Especially when the generated light has a substantial constant amplitude the use of photodiodes in combination with low frequency electronic circuits provides an economic solution when multiple photodiodes are employed.

In order to carry out intensity measurements of the breast tissue the holder 45 comprises a first number of N input ports $I_1 \ldots I_N$ and a second number of M output ports $O_1 \ldots O_M$ whose positions relative to one another on the holder 45 are known. The input ports $I_1 \ldots I_N$ are coupled, via optical conductors $S_I \ldots S_N$, to the outputs of an input selection unit 44 whose input 50 is coupled to the light source 42 via an optical conductor 51. The output ports $O_1 \ldots O_M$ are coupled, via optical conductors $D_I \ldots D_M$, to the inputs of an output selection unit 46 whose output 49 is coupled to a photodetector 43 via an optical conductor 48. For example, 256 input ports and 256 output ports are used. Also other numbers are possible, for example 128 input ports and 128 output ports. It is remarked that the number of output ports M need not necessarily be equal to the number of input ports N. During measurement the input ports $I_1 \ldots I_N$ are coupled to the light source 42 and the output ports $O_1 \ldots O_M$ are coupled to the photodetector 43. Coupling taking place in a specific order and the light being radiated into the turbid medium, via the input ports. A part of the light emanating from the turbid medium is conducted to the photodetector 43 via the output ports $O_1 \ldots O_M$ and the optical conductors $D_1 \ldots D_M$, the measured intensities being stored by the processing unit 41.

Subsequently, the processing unit 41 can derive an image of the internal structure of the turbid medium from the measured intensities. The image can subsequently be displayed on a monitor 47. The image is derived from the measured intensities using projection reconstruction. Projection reconstruction is known from X-ray computed tomography and is inter alia described in "Fundamentals of Image Processing" by A. K. Jain, Prentice Hall, 1989, pp. 439–441.

The resolution enhancement in accordance with the invention will be described in detail for a mammography device which comprises, for example an adaptation medium with a mirror. The mirror, having a reflection coefficient of, for example 0.9, is arranged on, for example, a mechanical device enabling adjustment of the distance between the turbid medium and the adaptation medium. This distance determines the effective reflection coefficient of the adaptation medium. A number of measurements are performed in order to derive an image of a region of an internal structure of the turbid medium which is situated between the light sources and the photodetectors. Enhancement of the resolution in accordance with the invention will be described with reference to FIG. 5. FIG. 5 shows a circular holder which accommodates the turbid medium; the circular holder comprises N input ports and N output ports which are provided along the circumference. The holder is made of a transparent material. For the purpose of illustration FIG. 5 shows only 8 input ports $I_i$ 52–59 and 8 output ports $O_i$ 60–67. FIG. 5 also shows the mirrors 68. Per measurement an intensity of the light originating from the selected input port $I_i$ is measured on a selected output port $O_j$ so as to be stored in the processing unit 41. Subsequently, N×N measurements are executed, all combinations of light sources and photodetectors then being measured with a first value $R_1$ of the effective reflection of the adaptation medium with respect to the turbid medium. After the execution of the measurements, N×N intensity values are then available for the reconstruction of an image. In accordance with the invention, the measurements are repeated for a second value $R_2$ of the effective reflection of the mirror, the heart line of the new photon path distribution then being situated approximately halfway between two heart lines of two photon path distributions of the preceding series of measurements. This effective reflection is adjusted by changing the distance between the mirrors and the holder. FIG. 5 shows the two heart lines $L_{ij}$ and $L_{i(j+1)}$ of two photon path distributions between a light source $S_i$ and a first photodetector $D_j$ and between the light source $S_i$ and a second photodetector $D_{j+1}$ for a first value of the effective reflection $R_1$. Furthermore, FIG. 5 shows the heart line $L_{ij}'$ of a photon path distribution associated with a source $S_i$ and a photodetector $D_j$, the value $R_2$ of the effective reflection then being chosen so that the center of the heart line $L_{i,j}'$ is situated approximately halfway between the heart line $L_{ij}$ and the heart line $L_{i(j+1)}$ or $L_{i(j-1)}$ (the latter is not shown in FIG. 5). After the execution of this second series of measurements, approximately more than N×N intensity values are then available for reconstruction. The processing unit 41 reconstructs an image of the internal structure of the turbid medium from these intensity values by projection reconstruction. This image can be displayed on the monitor 47. The resolution of the image thus obtained by means of the mammography device in accordance with the invention has been increased compared to an image obtained while utilizing the same number of light sources and photodetectors but not an adaptation medium.

For the adjustment of the light path $L_{i,j}'$ the value $R_2$ of the effective reflection of the adaptation medium can be determined, for example by executing calibration measurements in a turbid medium in which an object is arranged in a known position and by adjusting a known reflection of the adaptation medium; subsequently, an image of the internal structure is derived and the position of the object is determined from said image, after which the given position is compared with the known position so that the shift of the light path can be determined as a function of effective reflection.

Another possibility for adjusting the effective reflection in accordance with the invention consists in the use of an adaptation medium which comprises a liquid crystal device, acting as a filter, in combination with a mirror, e.g. a cholesteric mirror. Such a cholesteric filter, which can be part of a cholesteric mirror, is known from, inter alia, EP-A-643121. This principle is identical as described in relation with FIG. 5. In that case the cholesteric mirror, replaces the mirror 68, arranged besides the turbid medium in the holder 45 of the mammography device, thus achieving that the reflection coefficient R of the cholesteric mirror can be adjusted with respect to the turbid medium. The reflection coefficient of the cholesteric mirror is adjusted by applying an alternating voltage, originating from an external voltage source, across the cholesteric filter. This alternating voltage has a value in the range between approximately, 0 and 40 $V_{rms}$. This enables adjustment of the value of the reflection coefficient of the adaptation medium in a range between, for example 0.1 and 0.5. The shape of the cholesteric mirror can be adapted to some extent to the shape of the turbid medium, for example the breast of a female patient.

A cholesteric filter for use in a cholesteric mirror adaptable to the instant invention, generally comprises an optically active layer, which is situated between two substrates both provided with surface electrodes for applying an electric field. The optically active layer, which is in the cholesteric phase, comprises a three-dimensional polymer network which consists of the polymerization product of maximally 2 wt. % of monomers with at least two polymerizable groups and maximally 30 wt. % of liquid-crystalline monomers with one polymerizable group, and the rest of the optically active layer consists predominantly of a mixture of chiral and achiral liquid-crystalline molecules. An optically active layer of this composition can be switched in a simple and reproducible manner means of the electric field.

In a preferred embodiment, the filter comprises two flat, transparent substrates, for example of glass, which extend parallel to each other and are arranged at some distance from each other. The correct distance between the substrates is maintained by spacers, for example balls or fibers of uniform diameter which are present between the substrates. Each substrate is provided with a transparent surface electrode, for example of indium tin oxide, on the side facing the other substrate. Preferably, the substrates are also provided with an orientation layer, for example of rubbed polyamide or obliquely sputtered $SiO_x$. The edges of the substrates are provided with a packing strips. The substrates and the packing strip enclose a space which accommodates an optically active layer containing liquid-crystalline material which is in the cholesteric phase.

Figure 8:
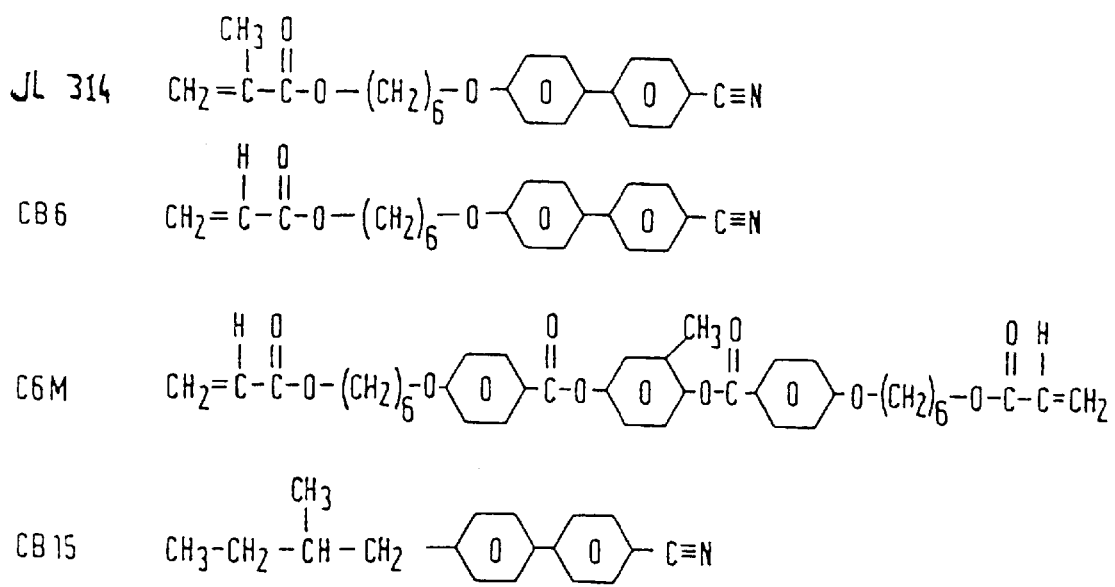
FIG. 8 shows structures of chemical compounds useful in a cholesteric mirror.

In the preferred embodiment, the optically active layer includes a mixture consisting of 0.1 wt. % of the diacrylate C6M, 19.0 wt. % of the monoacrylate JL314, 39.5 wt. % of the non-reactive chiral CB15, and 40.5 wt. % of the non-reactive achiral B1006. The chemical structural formulas which correspond are described in FIG. 8. B1006 is produced by Merck, and contains fluorine-substituted and/or chlorine-substituted cyanobivinyl and cyanotervinyl compounds. A quantity of 1 wt. % of the photoinitiator Igacure 651 was added to this mixture. After the mixture has been provided between the substrates (spaced apart by 2.7 micrometers) the mixture is polymerized by means of a UV light source (wavelength 366 nm).

In use, the preferred embodiment of the cholesteric filter has a transmission peak at room temperature at a wavelength of approximately 550 nm. This transmission peak is substantially unchanged from no electric field up to a field intensity due to application of a potential difference of approximately 30 V between the surface electrodes. At higher field intensities, the intensity of the transmission peak decreases rapidly. At a field intensity due to application of 45 V, the peak substantially disappears. When the electric field reduced to below 30 V or removed, the original transmission peak at 550 nm is immediately restored. Switching between both extreme states, i.e., between 30 V and 45 V, can be repeated many times without the occurrence of an important change in the transmission spectra. Hysteresis does not occur.

Another possibility is to employ a mirror with an switchable reflection coefficient as described in international patent application PCT/IB 96/00365.

Such mirrors can be constructed from thin layers of trivalent metals that can reversibly form trihydrides and can exhibit a metal-semiconductor transition. These metals include yttrium, scandium, lanthanum, and the rare earth metals with atomic numbers from 58 through 71. A preferred mirror comprises: a substrate, such as glass, quartz, diamond, or aluminum oxide; a switching film of yttrium of from 100 to 1000 nm thickness, and preferably 500 nm thickness; and a thin catalytically-active layer of palladium of from 2 to 25 nm thickness, and preferably 5 nm thickness. The palladium serves to promote the dissociation of molecular hydrogen into atomic hydrogen.

A preferred mirror can be constructed as follows. The switching film can be applied to a substrate by means of conventional methods such as vacuum evaporation, sputtering, laser ablation, chemical vapor deposition, or electroplating. It is important that during and after application of the switching film, the metal of the switching film is not subject to oxidation. In a vacuum-evaporation process, this is achieved by maintaining the pressure, in particular of the residual gasses, water, and oxygen, at a low level below $10^{-6}$ to $10^{-7}$ mbar. The catalytically-active layer, for example palladium, can alternatively be applied by means of one of the above-mentioned methods.

A preferred mirror can be used as follows. The deposited metal switching film is first exposed to molecular hydrogen at a pressure of 1 bar at room temperature in a cell shut off from the environment. The palladium layer forms atomic hydrogen, which is subsequently absorbed in the switching film. After 5 seconds, the initially non-transparent mirror-like switching film has been converted to a transparent light yellow film having a transmission of approximately 20%. The film formed comprises semiconductive $YH_3$ with a bandgap of 2.3 ev. Subsequently the cell is evacuated to a pressure of 1 mbar, whereafter air is admitted up to a pressure of 1 bar. The transparent switching film is subsequently heated to 70° C. Within five seconds, the switching film has become mirror-like again and comprises metallically conducting $YH_2$. The mirror-like film of $YH_2$ can be converted to a transparent switching film of $YH_3$, within five seconds by exposure to hydrogen. The conversion of $YH_2$ to $YH_3$, and the reverse, is reversible.

Another possibility of enhancing the resolution of the image formed by the mammography device in accordance with the invention consists in using a liquid adaptation medium in the holder; for the second series of measurements use is then made of a liquid adaptation medium having an absorption coefficient $\mu_{a2}$ and transport or reduced scattering coefficient $\mu_{s2}'$ which deviate from the absorption coefficient $\mu_{a1}$ and the transport or reduced scattering coefficient $\mu_{s1}'$ of the liquid adaptation medium used for the first series of measurements. For example, by dilution of the liquid or adding of dyes. The absorption coefficient $\mu_a$ and the transport or reduced scattering coefficient $\mu_s'$ of the liquid being chosen so that the heart line $L_{ij}$ associated with a source $S_i$ and a photodetector $D_j$ is situated substantially halfway between the heart line $L_{ij}$ and the line $L_{i(j+1)}$ or $L_{i(j-1)}$ of the first series of measurements as mentioned in the description of FIG. 5.

The device according to the invention can be provided with different types of holders for various measurement geometries. The holders are described in relation to FIG. 6 and FIG. 7.

Figure 6:
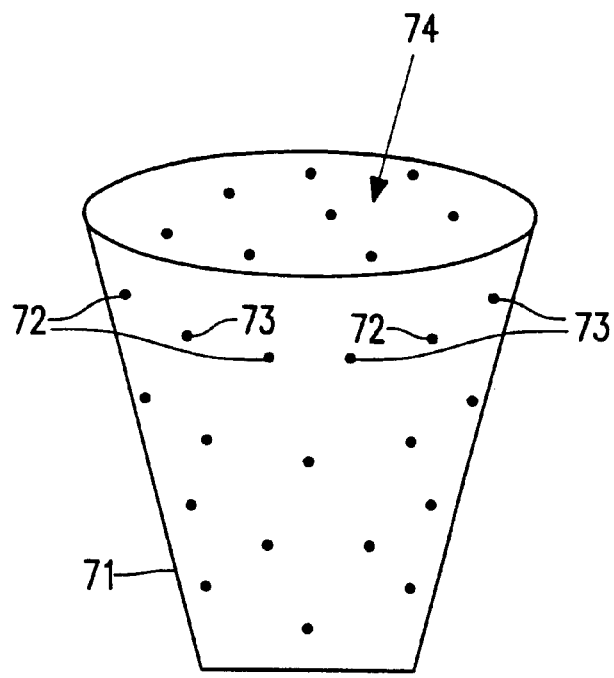
FIG. 6 shows a first type of holder of the mammography device for carrying out measurements by means of a fan beam geometry.

FIG. 6 shows an example of a holder of the mammography device 40 which is intended to receive a liquid adaptation medium. The holder 70 is intended to carry out an in vivo measurement with a fan-shaped beam geometry in the mammography device 40. The holder 70 comprises a bowl-shaped or conical part 71 for receiving a liquid adaptation medium and a part of a breast of a female. In the wall of the bowl-shaped part there are provided N input ports and M output ports, said ports being arranged in circles. This is illustrated in FIG. 6, showing three input ports 72 and three output ports 73 arranged on a circle. In practice a holder of the first type may comprise 128 or 256 input ports and output ports. The spacing of the input ports and the output ports must be known for the reconstruction of an image and preferably remains constant during performing the measurements. The holder 70 can be coupled to the mammography device 40 by means of optical conductors. The input ports $I_j$ ... $I_N$ can then be coupled to the light source 42 via optical conductors $S_1$ to $S_N$ and the input selection unit 44. The output ports $O_1$ ... $O_M$ can be coupled to the photodetector 43 via the optical conductors $D_1$ to $D_N$, the output selection unit 46 and the optical conductor 48. For the liquid adaptation medium use can be made of, for example a intralipid solution or a commercially available suspension for cosmetic use, a so called body-milk. For the execution of the measurements the input ports and output ports can be chosen so that a two-dimensional or three-dimensional image of the internal structure can be derived from the measured intensities.

Figure 7:
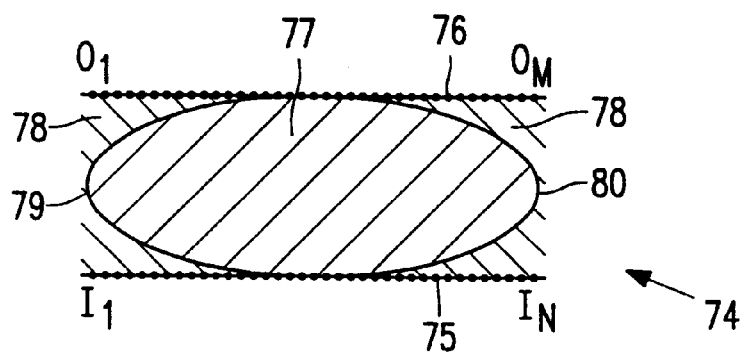
FIG. 7 shows a second type of holder of the mammography device for carrying out measurements with a parallel plate geometry.

A further holder suitable for use in the mammography device 40 is, for example, a holder for performing measurements with a parallel plate geometry. FIG. 7 is a plan view of such a holder 74. The holder comprises two substantially parallel transparent plates 75, 76 which are arranged around the breast 77 of a female patient. This results in an image of a parallel plate geometry with a slab thickness of approximately 6 cm. The breast can be compressed, for example in a mediolaterial or a craniocaudal direction by the plates 75, 76. A first plate 75 of the holder 74 comprises a number of N input ports $I_1$ to $I_N$ for the coupling of optical conductors $S_1$ to $S_N$ and the other transparent plate 76 comprises a second number of M output ports for the coupling of the optical conductors $D_1$ ... $D_M$. The optical conductors $S_1$ ... $S_N$, $D_1$ ... $D_M$ can be coupled to the input selection unit 44 and the output selection unit 46, respectively. The space between the plates and besides the breast is filled with the liquid adaptation medium 78.

Another possibility to employ the liquid adaptation medium is the use of a bag of transparent synthetic material which comprises the liquid adaption medium. This bag can be placed between the holder and the breast. The advantage of this bag is that it avoids the loss of any liquid and it could be more comfortable for the woman which is examined.

I claim:

1. A method for forming an image of a turbid medium comprising:

irradiating a turbid medium by means of light emanating from a light source at a plurality of positions, wherein the turbid medium is disposed with respect to an adaptation medium so that one or more adjustable optical properties of the adaptation medium can influence a photon path distribution in the turbid medium, adjusting said one or more optical properties of the adaptation medium to one or more first values resulting in a first photon path distribution in the turbid medium, measuring a first set of intensities of the light emanating from the turbid medium at a plurality of positions, adjusting said one or more optical properties of the adaptation medium to one or more second values resulting in a second photon path distribution in the turbid medium, measuring a second set of intensities of the light emanating from the turbid medium at the plurality of positions, and reconstructing an image of the turbid image from the first and second set of measured intensities.

2. A method as claimed in claim 1 wherein the adaptation medium comprises a liquid.

3. A method as claimed in claim 2 wherein the one or more optical properties of the adaptation medium are adjusted by adding a dye to the liquid.

4. A method as claimed in claim 2 wherein the liquid comprises a commercially available suspension for cosmetic purposes.

5. A method as claimed in claim 1 wherein the one or more adjustable optical properties of the adaptation medium are selected from a set consisting of a variable reflection coefficient with respect to the turbid medium, an absorption parameter, and a scattering parameter.

6. The method of claim 1 wherein said irradiating comprises irradiating with light of a substantially constant intensity.

7. A device for forming an image of a turbid medium comprising:

a holder adapted to receive the turbid medium and an adaptation medium which are mutually disposed so that one or more adjustable optical properties of the adaptation medium can influence a photon path distribution in the turbid medium, a light source for irradiating the turbid medium with light at a plurality of positions, a photodetector for measuring a set of intensities of light emanating from the turbid medium at a plurality of positions, and a processing unit configured for deriving an image of the turbid medium from a first set and a second set of measured intensities, wherein the first set of intensities is measured after adjusting said one or more optical properties of the adaptation medium to one or more first values resulting in a first photon path distribution in the turbid medium, and wherein the second set of intensities is measured after adjusting said one or more optical properties of the adaptation medium to one or more second values resulting in a second photon path distribution in the turbid medium.

8. A device as claimed in claim 7 wherein the adaptation medium comprises a liquid.

9. A device as claimed in claim 7 wherein the light source is adapted to generate light having a substantially constant intensity.

10. A method as claimed in claim 7 wherein the one or more adjustable optical properties of the adaptation medium are selected from a set consisting of a variable reflection coefficient with respect to the turbid medium, an absorption parameter, and a scattering parameter.

11. A device for forming an image of a turbid medium comprising:
- a holder adapted to receive the turbid medium and an adaptation medium which are mutually disposed so that an adjustable reflection coefficient of the adaptation medium with respect to the turbid medium can influence a photon path distribution in the turbid medium,
- a light source for irradiating the turbid medium with light at a plurality of positions,
- a photodetector for measuring a set of intensities of light emanating from the turbid medium at a plurality of positions, and
- a processing unit configured for deriving an image of the turbid medium from a first set and a second set of measured intensities, wherein the first set of intensities is measured after adjusting said reflection coefficient of the adaptation medium to a first value resulting in a first photon path distribution in the turbid medium, and wherein the second set of intensities is measured after adjusting said reflection coefficient of the adaptation medium to a second value resulting in a second photon path distribution in the turbid medium.

12. A device as claimed in claim 11 wherein the adaptation medium comprises a cholesteric including a liquid crystal device acting as a filter of adjustable transmissivity.

13. A device as claimed in claim 11 wherein the light source is adapted to generate light having a substantially constant intensity.

14. The device of claim 11 wherein the adaptation medium comprises a mirror including a switching film switchable between a first state which is metallic and substantially reflecting and a second state which is semi-conductive and substantially transparent.

* * * * *